United States Patent [19]

Hori et al.

[11] Patent Number: 4,832,504

[45] Date of Patent: May 23, 1989

[54] METHOD FOR MEASURING SURFACE TEMPERATURE OF SENSORS

[75] Inventors: Tomoshige Hori, Kitamoto; Kensuke Itoh, Kodaira, both of Japan

[73] Assignee: Snow Brand Milk Products Co., Ltd., Japan

[21] Appl. No.: 157,261

[22] Filed: Feb. 18, 1988

[30] Foreign Application Priority Data

Mar. 6, 1987 [JP] Japan ................. 62-51520

[51] Int. Cl.$^4$ ................. G01K 7/00
[52] U.S. Cl. ................. 374/183; 374/163; 374/3; 374/185; 174/113 C; 174/131 A
[58] Field of Search ................. 374/1, 3, 163, 183, 374/184, 185; 174/113 C, 131 A

[56] References Cited

U.S. PATENT DOCUMENTS

| | | | |
|---|---|---|---|
| 3,216,236 | 11/1962 | Rohrbach | 374/3 |
| 3,530,718 | 10/1967 | Ehlo | 374/183 |
| 4,050,289 | 9/1977 | Fairbairn et al. | 374/3 |
| 4,536,851 | 8/1985 | Germanton et al. | 374/183 |

Primary Examiner—William A. Cuchlinski, Jr.
Assistant Examiner—Diego F. F. Gutierrez
Attorney, Agent, or Firm—Griffin, Branigan & Butler

[57] ABSTRACT

A method for measuring a surface temperature of a sensor being heat-transferably contacted with a subject fluid by employing an electrically heating method in which the surface temperature is measured while passing an electrical current through an electrical conductor included in said sensor. In this measuring method, the surface temperature is expressed as a function of a specific value inherent in the sensor, an amount of the electric current supplied to the electrical conductor, and a temperature of the electrical conductor. The sensor is heat-transferably contacted with another fluid whose physical properties are previously known, a surface temperature of the sensor contacted with the another fluid is determined by satisfying a relational equation between the physical properties of the another fluid and the surface temperature, and the specific value inherent in the sensor is determined by using the determined surface temperature. The surface temperature of the sensor contacted with the subject fluid is measured by using the determined specific value inherent in the sensor. Therefore, various physical properties of the subject fluid can be precisely measured even if the theoretically determined specific value of sensor is different from the actual specific value.

9 Claims, 1 Drawing Sheet

METHOD FOR MEASURING SURFACE TEMPERATURE OF SENSORS

BACKGROUND OF THE INVENTION

The present invention relates to a method for measuring a surface temperature of a sensor, and more particularly to such a method employing an electrical heating method for measuring various physical properties of fluids.

Generally, it is very important for a process control of a fluid to measure physical properties of the fluid (for example kinematic viscosity).

In Japanese Patent laid-open application 60 (1985)-152,943, there is disclosed a method for measuring physical properties of a fluid by using a thin metal wire as a sensor by putting the thin metal wire into a fluid as a measuring object, charging the thin metal wire with electricity so as to add heating to the sensor and then calculating a heat transfer coefficient on the surface of the thin metal wire.

In the above mentioned method, because a heat-transfer coefficient is calculated from the function of a surface temperature of a sensor, the precise measurement of a surface temperature of a sensor is of great importance.

Recently, various kinds of sensing devices have been used. Especially, the abovementioned thin metal wire sensors have difficulties in the durability and the strength.

Thus a multiple layer sensor coated with an insulated membrane on the surface of a thin metal wire has been employed to improve that durability and strength.

However, in the prior art, no method has been known for precisely measuring a surface temperature of such a multiple layer sensor without direct contact of a temperature sensing device to the surface of the multiple layer sensor. This contact with the temperature sensing device will, however, result in the usual significant changes of the surface temperature of the multiple layer sensor and, of course, give false measurements.

SUMMARY OF THE INVENTION

It is therefore an object of the present invention to provide a method for measuring precisely a surface temperature of a sensor even when the sensor is a multiple layer sensor and without the use of a temperature sensing device.

According to the present invention, this aim is achieved by a method for measuring a surface temperature of a sensor which is heat-transferably contacted with a subject fluid by employing an electrical heating method in which the surface temperature is measured while passing an electrical current through an electrical conductor embedded in the sensor.

In this method of measuring a surface temperature of a sensor, the surface temperature is expressed as a function of a specific value inherent in the sensor, an amount of the electric current supplied to the electrical conductor, and a temperature of the electrical conductor.

The specific value inherent in the sensor is determined by the steps of:

(i) heat-transferably contacting the sensor to another fluid whose physical properties are previously known;

(ii) determining a surface temperature of the sensor in contact with the another fluid by satisfying a relational equation between the known physical properties of the another fluid and the surface temperature;

(iii) determining the specific value inherent in the sensor, by using the determined surface temperature; and then calculating a surface temperature of the sensor when in contact with a different subject fluid by using the determined specific value inherent in the sensor.

In accordance with the present invention, the surface temperature is expressed as a function of a specific value inherent in the sensor, an amount of the electric current supplied to the electrical conductor, and a temperature of the electrical conductor.

Therefore, the surface temperature of the sensor can be calculated from the directly measured amount of the electric current supplied to the electric conductor and the temperature of the electric conductor, and with the obtained specific value inherent in the sensor.

This specific value inherent in the sensor can be theoretically obtained as an analytical solution calculated in regard to the sensor's designed structural geometry.

In most existing sensors, however, their actual specific values are different from the theoretical specific values as calculated from analytical solutions of the designed structural geometry because of many factors, and especially manufacturing tolerance, etc. The difference between the actual and theoretical specific values results in inaccurate measurements of a surface temperature of the sensor.

In the measuring method according to the present invention, an actually manufactured sensor, as opposed to a theoretically geometric design, is heat-transferably contacted with the fluid whose physical properties are previously known. A surface temperature of the sensor when contacted with the known fluid is determined by satisfying a known relational equation between the physical properties value of the fluid and the surface temperature, and the specific value inherent in the sensor is determined by using the determined surface temperature.

Accordingly the actual specific value inherent in manufactured sensors can be accurately calculated, and therefore a surface temperature of the sensors can be accurately calculated when measuring unknown physical properties of subject fluid.

Thus, the precise measurement of a surface temperature of a sensor permits the accurate measurement of the fluid's physical properties, such as kinematic viscosity.

Other and further objects, features and advantages of the present invention will appear more fully from the following description.

DETAILED DESCRIPTION OF THE INVENTION

Figure 1:
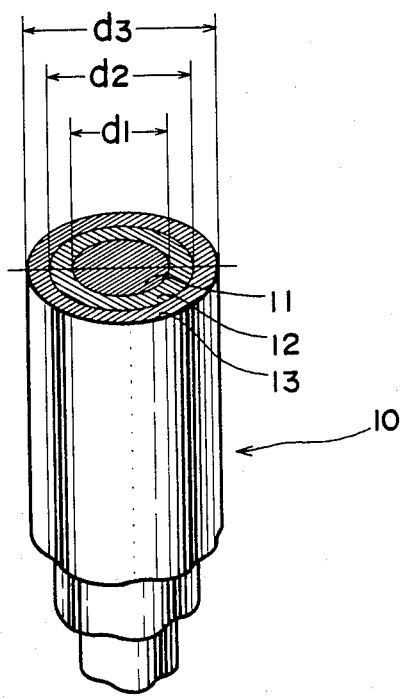
FIG. 1 illustrates a transverse sectional view in perspective of a multiple layer sensor embodying the present invention.

The invention will now be described by way of example with reference to the accompanying drawings.

As illustrated in FIG. 1, an embodiment of the invention is shown as in a triple-layer sensor 10. Sensor 10 comprises a cylindrical non-heating core element 11 having a diameter $d_1$, a tubular heating element 12 having an inner diameter $d_1$, an outer diameter $d_2$ and a thermal conductivity $\lambda_2$, and a nonheating outer tubular element 13 having an inner diameter $d_2$, an outer diameter $d_3$ and a thermal conductivity $\lambda_3$.

The determination of a surface temperature of this sensor 10 will be discussed below.

Fourier's heat conduction equation is represented by the following Equations (1).

$$\frac{\partial \theta}{\partial t} = a \nabla^2 \theta + \frac{W}{C\rho} \tag{1}$$

Laplacian operator $\nabla^2$ appearing in Equation (1) is expressed as follows, in cylindrical coordinates.

$$\nabla^2 = \frac{\partial^2}{\partial r^2} + \frac{1}{r}\frac{\partial}{\partial r} + \frac{1}{r^2}\frac{\partial^2}{\partial \phi^2} + \frac{\partial^2}{\partial z^2} \tag{2}$$

where
r: distance in the radial direction
$\phi$: rotatory angle of r-axis
Z: vertical distance If the cylinder is vertical and heat transfers at the two ends of the cylinder can be ignored, in Equation (2), we obtain, $$\nabla^2 = \frac{d^2}{dr^2} + \frac{1}{r}\frac{d}{dr} \tag{2'}$$

Substituting $d_3/2$ for r in the steady-state solution of Equation (1) in which $\nabla^2$ is as Equation (2)', we obtain a surface temperature of outer tube 13, that is a surface temperature $\theta_s$ of the sensor, as an analytical solution of Fourier's heat conduction equation as follows.

$$\theta_s = \theta_w - W \left[ \frac{d_2}{8\lambda_3}(d_3 - d_2)\left\{1 - \left(\frac{d_1}{d_2}\right)^2\right\} + \right. \tag{3}$$

$$\frac{d_2^2}{16\lambda_2} - \frac{d_1^2}{8\lambda_2} \log \frac{d_2}{2} +$$

$$\frac{1}{8\lambda_2(d_2^2 - d_1^2)} \left\{ d_1^4 \left( \frac{3}{4} - \log \frac{d_1}{2} \right) + \right.$$

$$\left. \left. d_1^2 d_2^2 \left( \log \frac{d_2}{2} - \frac{1}{2} \right) - \frac{1}{4} d_2^4 \right\} \right]$$

where
$\theta_w$: average temperature of heating element 12
W: heat generated in the unit volume of element 12 (Both $\theta_w$ and W can be directly measured as explained above.)

Since thermal conductivity $\lambda_2$ of heating element 12 which is made of metals is significantly larger, e.g. by 1000 times or more, then thermal conductivity $\lambda_3$ of non-heating element 111, made of, for example, synthetic resin, $\lambda_3/\lambda_2$ can be considered as zero.
Hence $$\theta_s = \theta_w - \frac{Wd_2}{8\lambda_3}(d_3 - d_2)\left\{1 - \left(\frac{d_1}{d_2}\right)^2\right\} \tag{4}$$

$$\therefore \lambda_2 \gg \lambda_3$$

Even if there is a thermal conductor such as metal membrane coating the surface of outer tube 13, the $\lambda_3/\lambda_2$ value can still be considered as zero value.

By, expressing value W in Equation (4) in terms of the electrical current i passing through heating element 12 by means of a relational equation therebetween, separating into two terms, i.e. specific and variable terms, and rearranging the terms of the formula for the surface temperature $\theta_s$ of the sensor can be written in the form $$\theta_s = \theta_w - \frac{R_0 i^2 (d_3 - d_2)(1 + \alpha_w \theta_w)}{2\pi l \lambda_3 d_2} \tag{5}$$

$$= \theta_w - A \cdot i^2 (1 + \alpha_w \theta_w)$$

where
$R_0$: electrical resistance of the heating element at 0° C.
$\alpha_w$: temperature coefficient of the electrical resistance
l: length of the sensor $$A = \frac{R_0(d_3 - d_2)}{2\pi l \lambda_3 d_2} \tag{6}$$

Specific value A in Equation (6) is, therefore, the inherent in the sensor, and is theoretically obtained as an analytic solution calculated from the sensor's structural configuration. More specifically, specific value A is represented in terms of $R_0$, $d_3$, $d_2$, e, $\lambda_3$, which are determined according to the sensor's structural configuration. As for $\theta_s$, electrical current i supplied to heating element 12 and temperature $\theta_w$ of heating element 12, these can be directly measured, and therefore surface temperature $\theta_s$ of the sensor can be calculated by using Equation (5).

In this manner, the theoretical specifical value of A in Equation (6) can be obtained. However, the actual specific values of existing sensors are different from the theoretical specific value.

These difference are made by those heat transfers at the two ends which are not in the radial direction, manufacturing tolerance of the sensor, etc.

Accordingly, in this embodiment, to correct the error between the theoretical and actual specific values, an existing sensor is heat-transferably contacted with fluid whose physical properties are previously known, a surface temperature of the sensor in contact with the fluid is determined by satisfying a relational equation between the physical properties of the fluid and the surface temperature, and the actual specific value in Equation (6) inherent in the sensor is determined by using the determined surface temperature.

Thus, representing the theoretical specific value of a sensor by A, the actual specific value inherent in the manufactured sensor by $A_{exp}$, and a correction factor by K, the following formula is provided.

$$A_{exp} = K \cdot A \tag{7}$$

The actual specific value $A_{exp}$ can be obtained by the steps of, heat-transferably contacting the actual sensor to fluid whose physical properties are previously known, determining a surface temperature of the sensor by satisfying a relational equation between the physical properties of the fluid and the surface temperature, and calculating the specific value A by using the determined surface temperature.

In case of employing pure distilled water as the fluid whose physical properties are previously known as functions of temperature, its kinematic viscosity $\nu$ can be expressed by the following formula.

$$\nu = f(\lambda, \beta, a, \theta_s, \alpha, \theta_\infty) \qquad (8-1)$$

for example, $$\nu^{2C1-C2} = C_0 g^{C1} S^{3C1-1} Q^{-1} \lambda \beta^{C-1} a^{-C2} (\theta_s - \theta_\infty)^{C1+1} \qquad (8-2)$$

where
- g: gravitational acceleration
- S: surface area of the sensor
- $\lambda$: thermal conductivity
- Q: total heat value generated in the sensor
- $\beta$: coefficient of volumetric expansion
- a: thermal diffusivity
- $\alpha$: coefficient of heat-transfer
- l: specific length of the sensor
- $\theta_\infty$: temperature of surrounding fluid
- $C_0, C_1, C_2$: constants in dimensionless heat transfer equation $$N_u = C_0 G_r^{C1} P_r^{C2} \qquad (8-3)$$

where $$Nu = \frac{ad}{\lambda}$$

$$Gr = \frac{l^3 g \beta (\theta_s - \theta_\infty)}{\nu^2}$$

$$Pr = \frac{\nu}{a}$$

$$a = \frac{W d_2}{4 \Delta \theta_s} \left\{ 1 - \left(\frac{d_1}{d_2}\right)^2 \right\} \qquad (8-4)$$

$$W = \frac{R_0 i^2 (1 + d_w \theta_w)}{\pi \left\{ \left(\frac{d_2}{2}\right)^2 - \left(\frac{d_1}{2}\right)^2 \right\} l} \qquad (8-5)$$

Then, determining $(\theta_s - \theta_\infty)$ so as to equalize the right side with the left side of Equation (8-2), the actual specific value $A_{exp}$ inherent in the existing sensor is obtained by using the determined value of $\Delta\theta_s$, as follows.

$$A_{exp} = (\theta_w - \theta_s)/i^2 (1 + \alpha_w \theta_w) \qquad (9)$$

Equation (7) is rewritten by $$K = (A_{exp})/A \qquad (10)$$

Substituting Equations (6) and (9) into Equation (10), the following formula is obtained.

$$K = \frac{2\pi l \lambda_3 d_2 (\theta_w - \theta_s)}{R_0 (d_3 - d_2) i^2 (1 + \alpha_w \theta_w)}$$

As described above, the specific value $A_{exp}$ of a existing sensor can be accurately calculated by the method according to the present invention. Therefore, a surface temperature of a sensor can be precisely calculated by a numerical method in the case of measuring unknown physical properties of subject fluids.

Although sensor 10 in the above explained embodiment is a heating element, it should be noted that the present invention can be applied to a sensor having an endothermic element instead of a heating element.

Although particular preferred embodiments of the invention have been disclosed in detail for illustration purposes, it should be recognized that variations or modifications of the disclosed invention lie within the scope of the present disclosure.

What is claimed is:

1. In a method for measuring a surface temperature of a sensor which is thermally contacted with a subject fluid and employing an electrical heating method in which said surface temperature is measured while passing an electrical current through an electrical conductor embedded in said sensor, the improvement comprising the steps of:

expressing said surface temperature ($\theta_s$) as a function of a specific value (A) inherent in said sensor, an amount of the electric current (i) supplied to said electrical conductor, and a temperature of said electrical conductor ($O_w$);

determining said specific value inherent in said sensor by the substeps of, (i) thermally contacting said sensor with another fluid whose physical properties are previously known, (ii) determining a surface temperature of said sensor in contact with said another fluid by satisfying a relational equation between said known physical properties of said another fluid and said surface temperature, and (iii) determining said specific value inherent in said sensor, by using the determined said surface temperature; and measuring said surface temperature of said sensor in contact with said subject fluid by using the determined said specific value inherent in said sensor.

2. A method according to claim 1 characterized in that said sensor comprises a multiple layer body including said electrical conductor.

3. A method according to claim 2 characterized in that said multiple layer body includes insulted membrane means on the surface of said electrical conductor.

4. A method according to claim 2 or claim 3, characterized in that said multiple layer body comprises a triple-layer structure including two non-heating elements inside and outside of said electrical conductor respectively.

5. A method according to claim 4 characterized in that said electrical conductor is tubular, and said multiple layer body comprises a cylindrical core element inside said electrical conductor and an outer tube outside said electrical conductor.

6. A method according to claim 2 or claim 3, characterized in that said multiple layer body comprises a cylindrical body.

7. A method according to claim 1, characterized in that said function of a specific value inherent in said sensor, an amount of the electric current supplied to said electrical conductor, and a temperature of said electrical conductor is a result of calculations of Fourier's heat conduction equation.

8. A method according to claim 1 or claim 7, characterized in that said another fluid whose physical properties are previously known comprises pure distilled water.

9. A method according to claim 1 or claim 7, characterized in that said step of determining said specific value inherent in said sensor comprises the substeps of
  (i) theoretically calculating said specific value inherent in said sensor by using Fourier's heat conduction equation,
  (ii) substituting said theoretical specific value with an unknown specific value, and
  (iii) calculating said unknown specific value by using said surface temperature determined with respect to said another fluid whose physical properties are previously known, said amount of the electric current supplied to said electrical conductor, and said temperature of said electrical conductor,
  and substituting the calculated unknown specific value for the said theoretically calculated specific value inherent in said sensor.

* * * * *